(12) United States Patent
Risi (10) Patent No.: US 7,881,811 B2
(45) Date of Patent: Feb. 1, 2011

(54) FLEXIBLE ELECTRODE ASSEMBLY HAVING VARIABLE PITCH ELECTRODES

(75) Inventor: Frank Risi, Newtown (AU)

(73) Assignee: Cochlear Limited, Macquarie University, NSW (AU)

( * ) Notice: Subject to any disclaimer, the term of this patent is extended or adjusted under 35 U.S.C. 154(b) by 977 days.

(21) Appl. No.: 11/605,960

(22) Filed: Nov. 30, 2006

(65) Prior Publication Data

US 2007/0135885 A1 Jun. 14, 2007

Related U.S. Application Data

(60) Provisional application No. 60/748,217, filed on Dec. 8, 2005, provisional application No. 60/748,273, filed on Dec. 8, 2005, provisional application No. 60/748,274, filed on Dec. 8, 2005, provisional application No. 60/748,314, filed on Dec. 8, 2005.

(51) Int. Cl.
*A61N 1/18* (2006.01)
(52) U.S. Cl. ...................................................... 607/137
(58) Field of Classification Search .................. 607/137
See application file for complete search history.

(56) References Cited

U.S. PATENT DOCUMENTS

| 4,284,856 | A | 8/1981 | Hochmair et al. |
| 4,648,403 | A | 3/1987 | Van Compernolle |
| 5,649,970 | A | 7/1997 | Loeb et al. |
| 6,074,422 | A | 6/2000 | Berrang et al. |
| 6,304,787 | B1 | 10/2001 | Kuzma et al. |
| 7,184,843 | B1 * | 2/2007 | Cohen .......................... 607/137 |
| 2002/0029074 | A1 * | 3/2002 | Treaba et al. ................ 607/137 |
| 2006/0161255 | A1 * | 7/2006 | Zarowski et al. .............. 623/10 |

FOREIGN PATENT DOCUMENTS

| WO | WO 96/31087 | 10/1996 |
| WO | WO 00/71063 A1 | 11/2000 |

OTHER PUBLICATIONS

Fu, et al., "Effects of Electrode Location and Spacing on Phoneme Recognition with the Nucleus-22 Cochlear Implant," Ear & Hearing, 1999.
Supplementary European Search Report for EP 00954176 dated May 27, 2004.
Hochmair-Desoyer, et al, "An Eight Channel Scale Tympani Electrode for Auditory Prostheses," IEEE Transactions in Biomedical Engineering, vol. BME-27, No. 1, pp. 44-50 (Jan. 1980).
International Search Report, PCT/AU00/01020, dated Oct. 9, 2000. 01.

* cited by examiner

*Primary Examiner*—Niketa I Patel
*Assistant Examiner*—Rex Holmes
(74) *Attorney, Agent, or Firm*—Kilpatrick Stockton LLP (57) ABSTRACT

An electrode assembly for use in a prosthetic hearing implant, the electrode assembly comprising: an elongate carrier member for implantation into the cochlea, the carrier member having a proximal end adapted to be positioned in a basal region of the cochlea, and a distal end adapted to be positioned in an apical region of the cochlea; and a plurality of electrodes disposed along a longitudinal surface of the carrier member, wherein the plurality of electrodes have a predetermined spacing to attain a desired flexibility along the length of the carrier member.

16 Claims, 9 Drawing Sheets

FLEXIBLE ELECTRODE ASSEMBLY HAVING VARIABLE PITCH ELECTRODES

CROSS-REFERENCE TO RELATED APPLICATIONS

The present application claims priority from U.S. Provisional Patent Application 60/748,217 entitled "Promoting Curvature and Maintaining Orientation In An Electrode Carrier Member Of A Prosthetic Hearing Implant," filed Dec. 8, 2005; U.S. Provisional Patent Application 60/748,273 entitled "Electrode Carrier Member Having An Embedded Stiffener For A Prosthetic Hearing Implant," filed Dec. 8, 2005; U.S. Provisional Patent Application 60/748,274 entitled "Electrode Carrier Member for a Prosthetic Hearing Implant Having Optical Length for Atraumatic Implantation," filed Dec. 8, 2005; and U.S. Provisional Patent Application 60/748,314 entitled "Electrode Carrier Member For A Prosthetic Hearing Implant Having Variable Pitch Electrodes To Facilitate Atraumatic Implantation," filed Dec. 8, 2005, all of which are hereby incorporated by reference herein.

BACKGROUND

1. Field of the Invention

The present invention relates generally to stimulating medical devices and, more particularly, to a flexible implantable electrode assembly for a stimulating medical device.

2. Related Art

Hearing loss is generally of two types, namely conductive and sensorineural. The treatment of both of types of hearing loss has been quite different, relying on different principles to deliver sound signals to be perceived by the brain as sound. Conductive hearing loss occurs when the normal mechanical pathways for sound to reach the hair cells in the cochlea are impeded, for example, by damage to the ossicles. In such cases, hearing loss is often improved with the use of conventional hearing aids, which amplify the sound so that acoustic information reaches the cochlear hair cells. Such hearing aids utilize acoustic mechanical stimulation, whereby the sound is amplified according to a number of varying techniques, and delivered to the inner ear as mechanical energy. This may be through a column of air to the eardrum, or through direct delivery to the ossicles of the middle ear.

On the other hand, sensorineural hearing loss is due to the absence or destruction of the cochlear hair cells which are needed to transduce acoustic signals into auditory nerve impulses. Individuals suffering from this type of hearing loss are unable to derive any benefit from conventional hearing aid systems regardless of the volume of the acoustic stimulus. This is because the natural mechanisms for transducing sound energy into auditory nerve impulses are either absent or damaged. In such cases, Cochlear™ implants (also referred to as Cochlear™ devices, Cochlear™ prostheses, Cochlear™ implant systems, and the like; simply "cochlear implants" herein) have been developed to provide the sensation of hearing to such individuals. In cochlear implants, electrical stimulation is provided via stimulating electrodes positioned as close as possible to the nerve endings of the auditory nerve, essentially bypassing the hair cells in a normally functioning cochlea. The application of a stimulation pattern to the nerve endings causes impulses to be sent to the brain via the auditory nerve, resulting in the brain perceiving the impulses as sound.

More recently, there has been an increased interest in Electro-Acoustical Stimulation (EAS) in which electrical stimulation of the cochlea is used in conjunction with acoustical stimulation. It is relatively common in hearing impaired individuals to experience sensorineural hearing loss for sounds in the high frequency range, and yet still be able to discern sounds in the middle to low frequency range, through the use of a conventional hearing aid, or naturally. Traditionally, in the majority of such cases, the recipient would only receive treatment to preserve and improve the hearing for the middle to low frequency sounds, most probably via a conventional hearing aid, and little would be done to attempt to restore the hearing loss for the high frequency sounds. This is due to the potential trauma caused by the implantation of an electrode assembly into the cochlea. Only if the individual lost the ability to perceive middle to low frequency sounds would consideration then be given to restoring the hearing loss for the high frequency sounds, in which case a cochlear implant would be considered a possible solution.

SUMMARY

In one aspect of the invention, an electrode assembly for use in a prosthetic hearing implant, the electrode assembly comprising: an elongate carrier member for implantation into the cochlea, the carrier member having a proximal end adapted to be positioned in a basal region of the cochlea, and a distal end adapted to be positioned in an apical region of the cochlea; and a plurality of electrodes disposed along a longitudinal surface of the carrier member, wherein the plurality of electrodes have a predetermined spacing to attain a desired flexibility along the length of the carrier member.

In another aspect of the invention, an electrode assembly for use in a prosthetic hearing implant is disclosed, the electrode assembly comprising: an elongate carrier member for implantation into the cochlea, the carrier member having a proximal end adapted to be positioned in a basal region of the cochlea, and a distal end adapted to be positioned in an apical region of the cochlea; and a plurality of electrodes disposed along a longitudinal surface of the carrier member, wherein a pitch of the plurality of electrodes varies over at least one portion of the elongate carrier member to attain a desired carrier member flexibility along the length of the carrier member.

BRIEF DESCRIPTION OF THE DRAWINGS

Embodiments of the present invention are described herein with reference to the following figures, in which.

DETAILED DESCRIPTION

Embodiments of the present invention are generally directed to an apparatus and method for facilitating implantation of a flexible electrode assembly of a stimulating medical device into a patient (also referred to herein as a recipient). Embodiments of the present invention are described below in connection with one type of stimulating medical device, a cochlear implant. Cochlear implants use direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear implant provides stimulation of the cochlear nucleus in the brainstem. Such devices, therefore, are commonly referred to as auditory brainstem implants (ABIs).

Exemplary embodiments of a cochlear implant include a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, the entire contents and disclosures of which are hereby incorporated by reference herein. It should be understood to those of ordinary skill in the art that embodiments of the present invention may be used in other stimulating medical devices such as neurostimulators, cardiac pacemakers/defibrillators, etc. as well as other medical devices which utilize an elongate carrier member to temporarily or permanently implant, deliver or otherwise introduce a therapeutic agent, sensor, device, etc. into a recipient.

Figure 1:
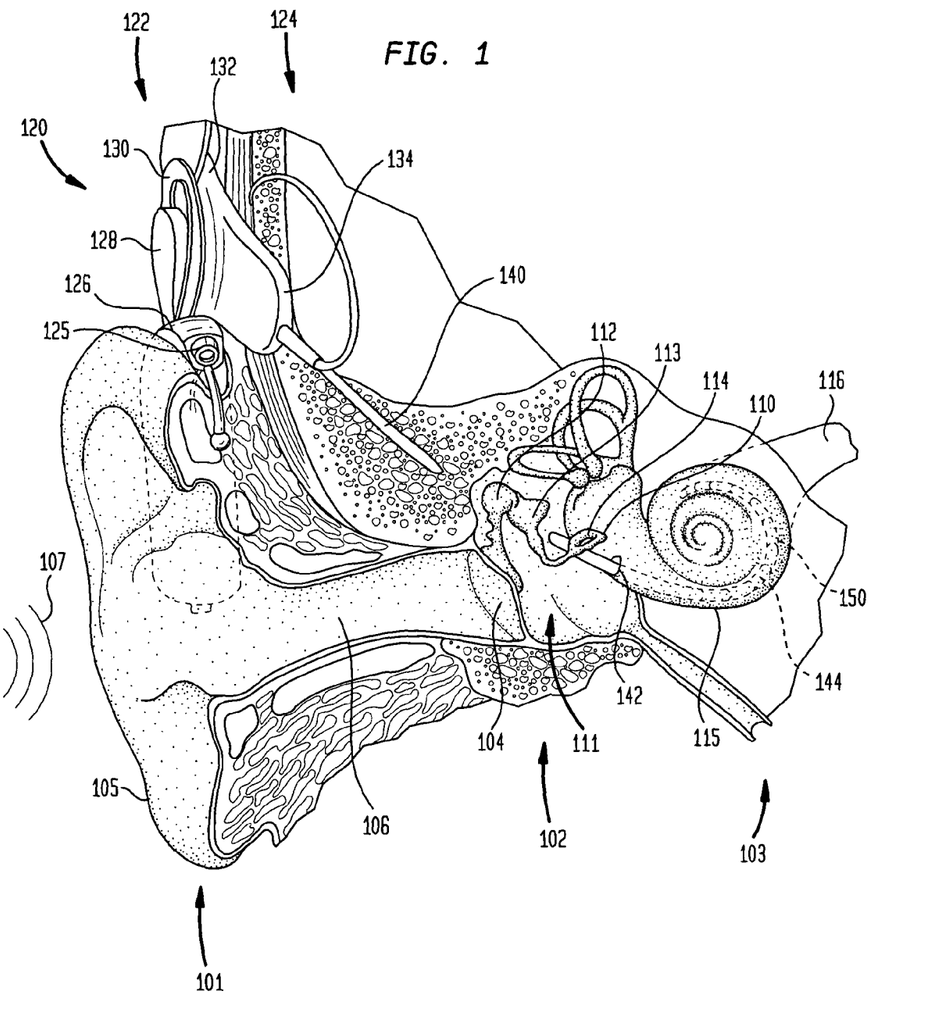
FIG. 1 is a perspective view of an implanted cochlear implant suitable for implementing embodiments of the present invention.

FIG. 1 is a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 104 which vibrates in response to acoustic wave 107. This vibration is coupled to oval window, or fenestra ovalis, 110 through three bones of middle ear 102, collectively referred to as the ossicles 111.

Ossicles 111 comprises the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells (not shown) to auditory nerve 116 and, ultimately, to the brain where they are perceived as sound. In some persons experiencing sensorineural hearing loss, there is an absence or destruction of the hair cells. Cochlear implant 120 is utilized to directly stimulate the ganglion cells to provide a hearing sensation to such persons.

FIG. 1 also shows how cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is provided to a behind-the-ear (BTE) speech processing unit 126 that generates coded signals. The coded signals are provided to an external transmitter unit 128, along with power from a power source (not shown) such as a battery. External transmitter unit 128 comprises an external coil 130 and, preferably, a magnet (not shown) secured directly or indirectly in external coil 130.

Internal component assembly 124 comprises an internal receiver unit 132 having an internal coil (not shown) that transcutaneously receives power and coded signals from external assembly 122, and provides such signals to a stimulator unit 134. In response to the coded signals, stimulator 134 applies stimulation signals to cochlea 115 via an implanted electrode assembly 140. Electrode assembly 140 enters cochlea 115 via a cochleostomy 142 or through oval window 110, and has an array 144 of one or more electrodes 150 positioned to be substantially aligned with portions of tonotopically-mapped cochlea 115. The delivery of stimulation signals at various locations along cochlea 115 causes a hearing percept representative of the received sound 107.

While cochlear implant 120 is described as having external components, in another embodiment, the controller, including the microphone, speech processor and power supply, may also be implantable. In such embodiments, the controller may be contained within a hermetically sealed housing or the housing used for stimulator unit 134.

Electrode assembly 140 preferably assumes an optimal electrode position in cochlea 115 upon or immediately following implantation into the cochlea. It is also desirable that electrode assembly 140 be configured such that the insertion process causes minimal trauma to the sensitive structures of cochlea 115. Usually electrode assembly 140 is pre-curved, held in a straight configuration at least during the initial stages of the implantation procedure, conforming to the natural shape of the cochlea during and subsequent to implantation.

Figure 2A:
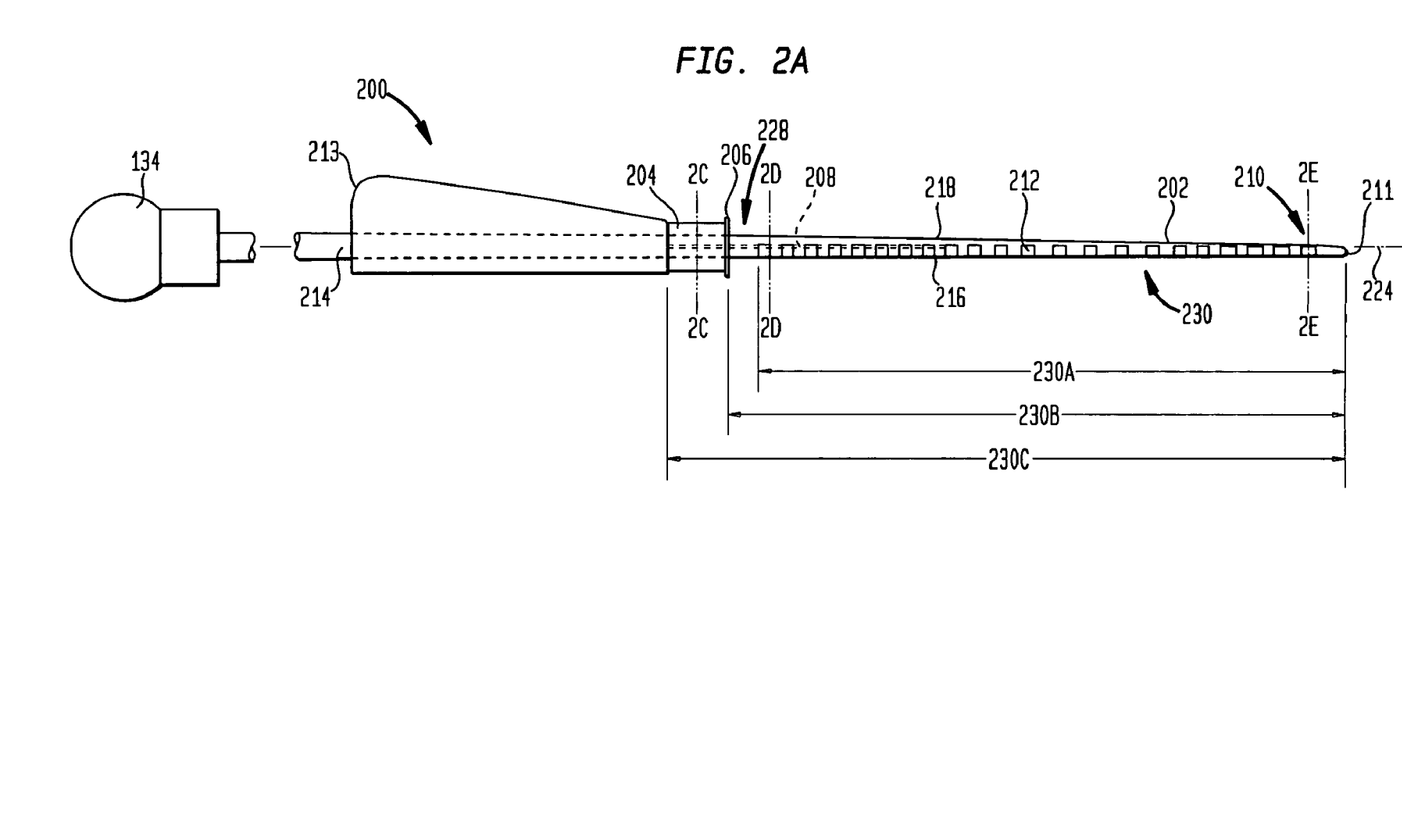
FIG. 2A is a side view of an electrode assembly in accordance with one embodiment of the present invention shown prior to insertion into a cochlea.
Figure 2B:
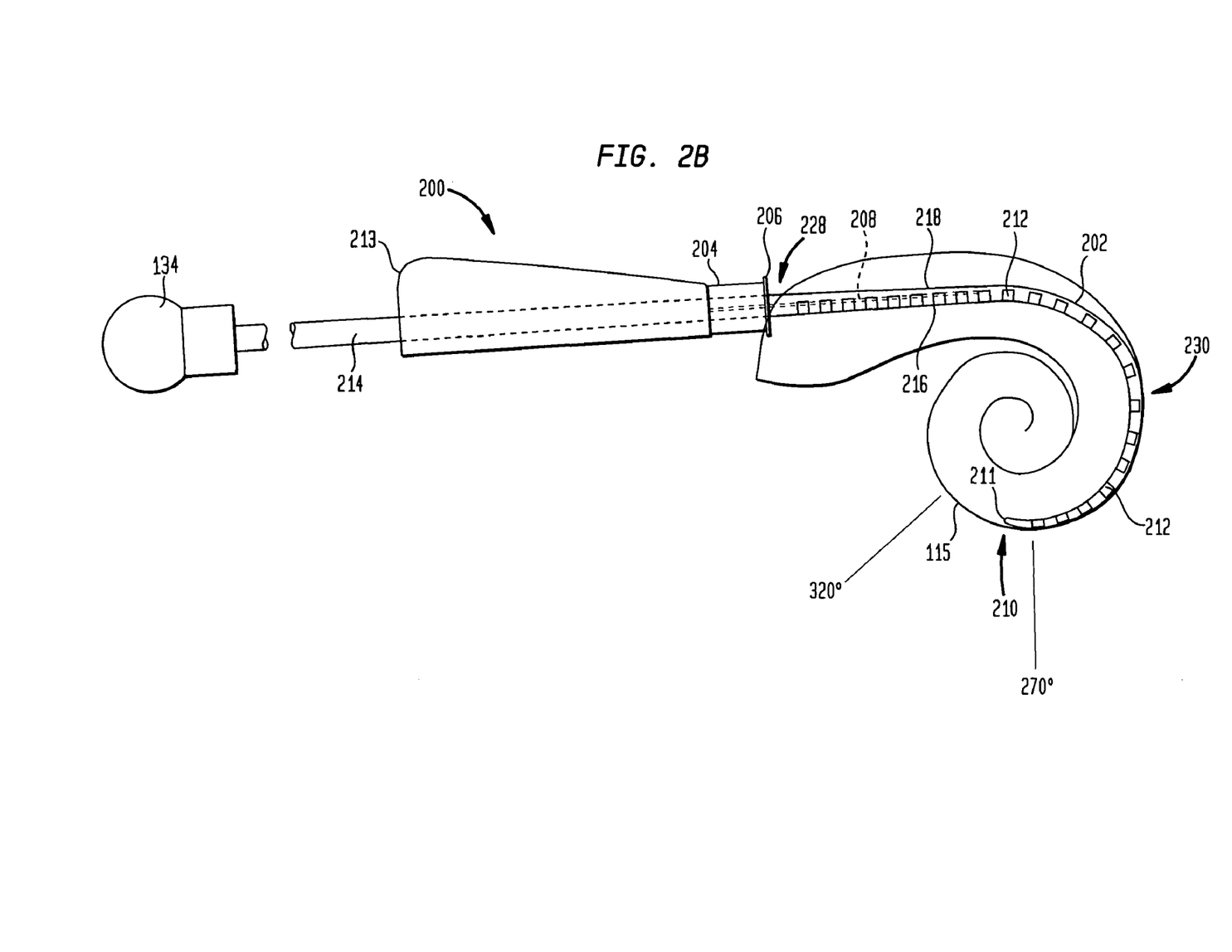
FIG. 2B is a side view of the electrode assembly of FIG. 2A, after implantation.
Figure 2C:
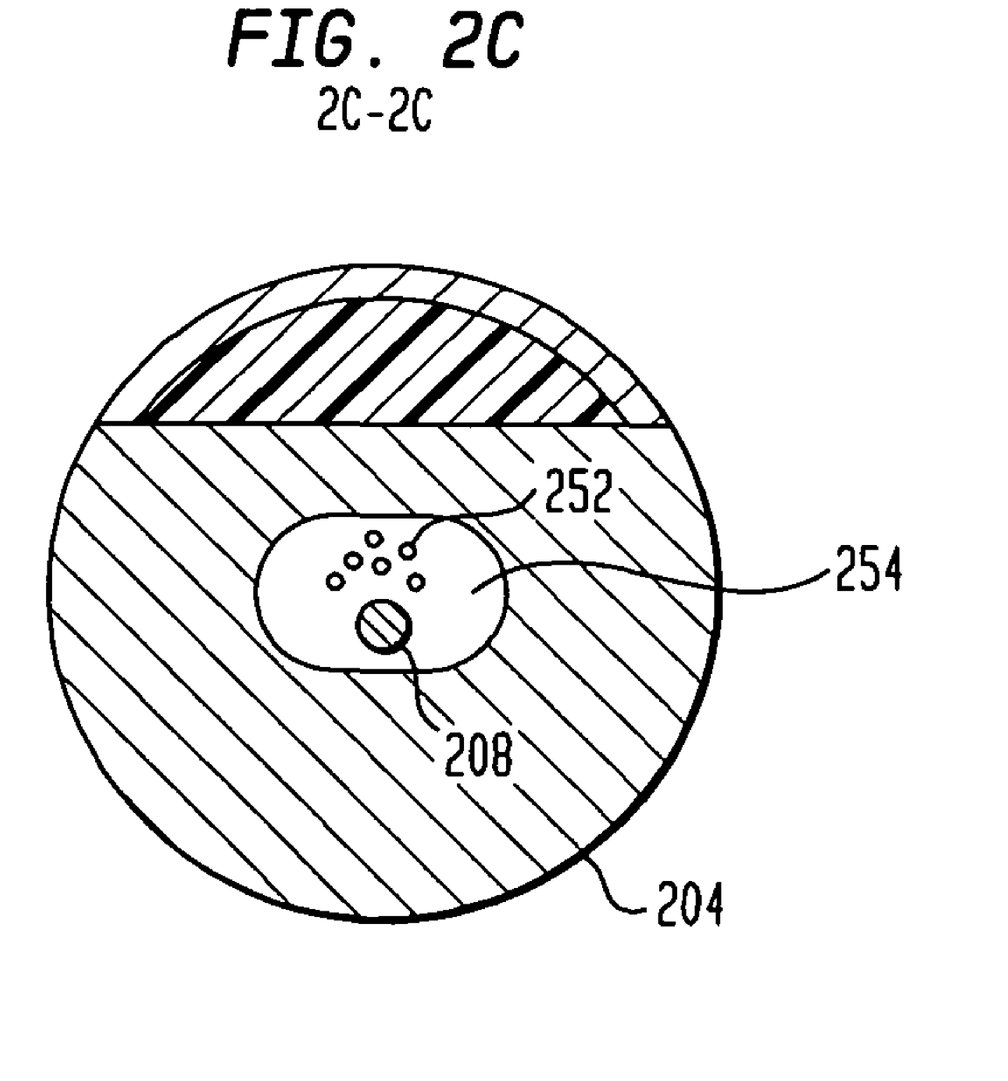
FIG. 2C is a cross sectional view of the electrode assembly of FIGS. 2A and 2B taken along section line 2C-2C in FIG. 2A.
Figure 2D:
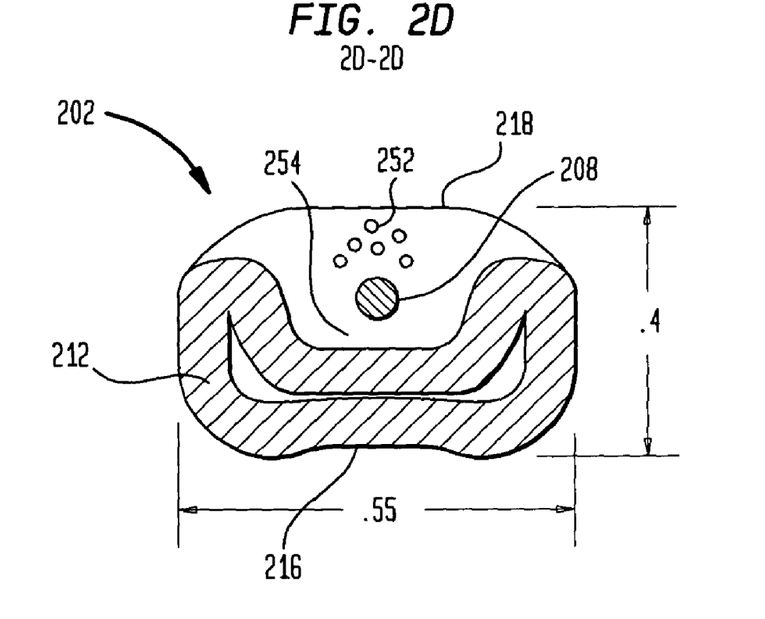
FIG. 2D is a cross sectional view of the electrode assembly of FIGS. 2A and 2B taken along section line 2D-2D in FIG. 2A.
Figure 2E:
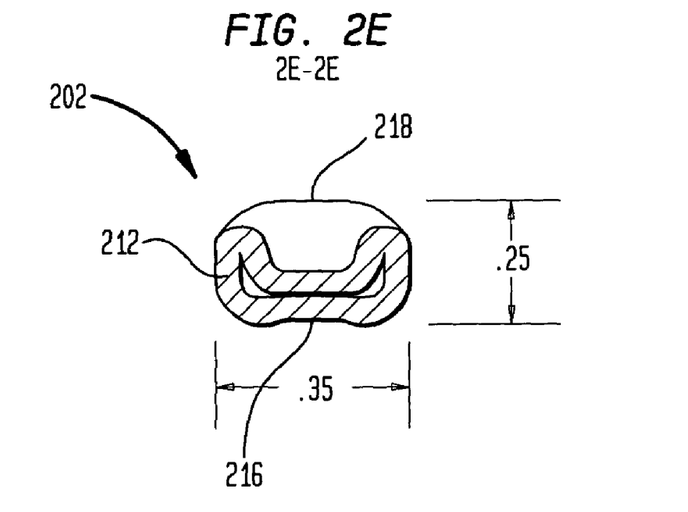
FIG. 2E is a cross sectional view of the electrode assembly of FIGS. 2A and 2B taken along section line 2E-2E in FIG. 2A.

FIGS. 2A and 2B are side views of one embodiment of electrode assembly 140, referred to herein as electrode assembly 200. In FIG. 2A, electrode assembly 200 is shown in a typical configuration prior to insertion into cochlea 115, while in FIG. 2B electrode assembly 200 is shown after insertion into cochlea 115. FIGS. 2C-2E are cross-sectional views of electrode assembly 200 taken along their respective section lines in FIG. 2A.

Electrode assembly 200 comprises a carrier member 202, a collar member 204, a holding member 213 and one or more leads 214. Carrier member 202 has a distal end 210 and a proximal end 228 connected to the distal end of laterally-extending collar member 204. The opposing proximal end of collar member 204 is connected to holding member 213. Lead 214 physically and electrically connects electrode assembly 200 and electrodes 212 disposed thereon with receiver/stimulator unit 134.

The surface of carrier member 202 which faces the interior of cochlea 115 when carrier member 202 is implanted in a recipient, is referred to herein as the medial surface 216 of carrier member 202. The opposing side of carrier member 202, referred to herein as lateral surface 218, faces the external wall and bony capsule (not shown) of cochlea 115 when carrier member 202 is implanted in a recipient. It should be understood that the terms medial surface, medial direction, and the like, are generally used herein to refer to the surfaces, features and directions toward the center of cochlea 115, while the terms lateral surface, lateral direction, and the like, are generally used herein to refer to surfaces, features and directions toward the exterior of cochlea 115.

A plurality of spaced-apart electrodes 212 are mounted on or in carrier member 202. The array of electrodes 212 is referred to herein as electrode array 230. Electrodes 212 may be disposed in a linear or non-linear array 230 on or in carrier member 202, and may be positioned to align with predetermined regions of tonotopically mapped cochlea 115. In alternative embodiments, electrodes 212 are implemented as described in the U.S. Provisional Patent Application 60/748, 217, 60/748,273 and 60/748,314, which are hereby incorporated by reference herein. Such arrangements allow for individual electrodes 212 to be utilized to stimulate selected regions of cochlea 115.

In one embodiment, electrodes 212 are half-band electrodes disposed in or on medial surface 216 of carrier member 202. It should be appreciated, however, that any electrodes now or later developed suitable for a particular application may be used in alternative embodiments of the invention. For example, in one alternative embodiment, electrodes 212 are banded electrodes extending substantially around the circumference of carrier member 202. In another embodiment, electrodes 212 do not laterally extend to or around the edges of carrier member 202. Typically, each electrode 212 is arranged such that its exposed surface is substantially parallel to a longitudinal axis 224 of carrier member 202. It should be appreciated, however, that electrode 212 may be implemented at other locations and orientations in alternative embodiments. It should further be appreciated that the quantity of electrodes 212 may vary from as few as one or two to as many as twenty-four or more.

In certain embodiments, at least one electrode 212 has a surface that is at least adjacent medial surface 216 of carrier member 202. Preferably, one or more electrodes 212 has a surface that is collocated with medial surface 216 of carrier member 202. In another embodiment, the surfaces of electrodes 212 are raised above or recessed into medial surface 216 of carrier member 202.

Electrodes 212 may be manufactured from a biocompatible conductive material such as platinum, although other materials or combinations of materials may be used. Alternatively, electrodes 212 may be coated with a biocompatible covering that does not interfere with transfer of stimulation signals to cochlea 115.

In this illustrative embodiment, each electrode 212 is electrically connected to at least one multi- or single-filament wire 252 (FIGS. 2C and 2D) that is embedded within flexible carrier member 202, collar member 204, handle member 213 and lead 214. In one embodiment, wires 252 are embedded in a volumetric core 254 of carrier member 202 and collar member 204. In an alternative embodiment, wires 252 may be located at or near surface 216 and/or surface 218 of carrier member 202. In other embodiments, wires 252 are embedded in different regions of carrier member 202 to facilitate curvature or to maintain orientation of carrier member 202 once it is implanted. It is through wires 252 that stimulator/receiver unit 134 (FIG. 1) provides electrical stimuli to selected electrodes 212. In one embodiment, wires 252 are connected to electrodes 212 by welding, although any suitable electrical connections now or later developed may be used.

It should be appreciated that the quantity of wires 252 connected to each electrode 212 may vary. For example, in one embodiment, at least two electrically conducting wires 252 are connected to each electrode 212. It should also be appreciated that suitable transmission means other than wires may be used to communicably couple receiver/stimulator unit 134 with electrodes 212. For example semiconductors or wireless technologies may be used.

In one embodiment, lead 214 extends from handle member 213 to stimulator 134 or at least the housing thereof. In one particular embodiment, lead 214 is continuous with no intermediate electrical connectors external the housing of stimulator unit 134; that is, there are no external connectors required to electrically connect electrode assembly 200 to stimulator 134. One advantage of this arrangement is that there is no requirement for a surgeon implanting electrode assembly 200 to make the necessary electrical connection between wires 252 extending from electrodes 214 and stimulator 134. Stimulator 134 is preferably encased within a housing that is implantable within the recipient, such as within a recess in the bone behind the ear posterior to the mastoid.

Returning to FIG. 2A, holding member 213 is configured to provide improved manual control of electrode assembly 200, and to identify electrode orientation. In alternative embodiments, holding member 213 may be configured as described in U.S. patent application Ser. No. 10/825,360, which is hereby incorporated by reference herein.

In certain embodiments, a profiled tip or tip region 211 is used to guide electrode assembly 200 during implantation in a manner that reduced friction. Alternative embodiments of tip region 211 are described in International Application PCT/US06/34010 entitled, "Elongate Implantable Carrier Member Having An Embedded Stiffener," and filed Aug. 31, 2006; U.S. patent application entitled "Prosthetic Hearing Implant Electrode Assembly Having Optimal Length for Atraumatic Implantation," filed concurrently under Ser. No. 11/605,952; and U.S. patent application entitled "Promoting Curvature and Maintaining Orientation of an Electrode Carrier Member of a Stimulating Medical Device," filed concurrently under Ser. No. 11/605,951 all of which are hereby incorporated by reference herein. In alternative embodiments, tip region 211 may be as described in U.S. patent application Ser. Nos. 10/825,358 and 11/125,171, which are also hereby incorporated by reference herein.

In certain embodiments, carrier member 202 also includes a stiffening member 208 permanently embedded in at least proximal region 228 of carrier member 202. Stiffening member 208 is embedded, for example, during the manufacture of carrier member 202. As shown in FIG. 2A, the illustrative embodiment of stiffening member 208 extends from an extracochlear position through collar member 204 and into carrier member 202. It should be appreciated that in alternative embodiments, stiffening member 208 need not be embedded in collar member 204, and may longitudinally extend further through carrier member 202 to terminate at any desired location along the length of electrode assembly 200. As best shown in FIG. 2B, the distance that stiffening member 208 extends into carrier member 202 is such that the stiffening member terminates just before the lateral wall of the first turn of cochlea 115 when carrier member 202 is completely inserted into cochlea 115.

Stiffening member 208 is configured to increase the stiffness of carrier member 202 in the region(s) of carrier member 202 in which stiffness member 208 is located. As such, stiffening member 208 assists in the prevention of buckling and/or deformation of carrier member 202 in such regions during insertion into cochlea 115. In particular, stiffener member 208 assists in maintaining proximal region 228 of carrier member 202 in a sufficiently straight configuration when subjected to the forces typically experienced during implantation. This allows carrier member 202 and electrodes 212 to be fully implanted into cochlea 115 without being subject to insertion forces that may damage the delicate structures of the cochlea.

Additionally, stiffening member 208 causes electrodes 212 to be positioned closer to the inner wall of cochlea 115, as generally a straight electrode will take a more lateral position in the basal region. As a result, the distance from the stimulating surface of carrier member 202 to the auditory nerve endings is substantially less than would be the case if stiffening element 208 were not embedded in electrode assembly 200. It is anticipated that this will provide similar benefits in the basal region as a perimodiolar electrode, such as the perimodiolar electrode described in U.S. Pat. No. 6,421,569, which is hereby incorporated by reference herein. It should also be appreciated that the stiffness of member 208 may be less than, the same, or greater than the stiffness of carrier member 202, so long as the presence of stiffening member 202 in regions of carrier member 202 results in at least one of such regions having a reduced likelihood of deformation.

Figure 3A:
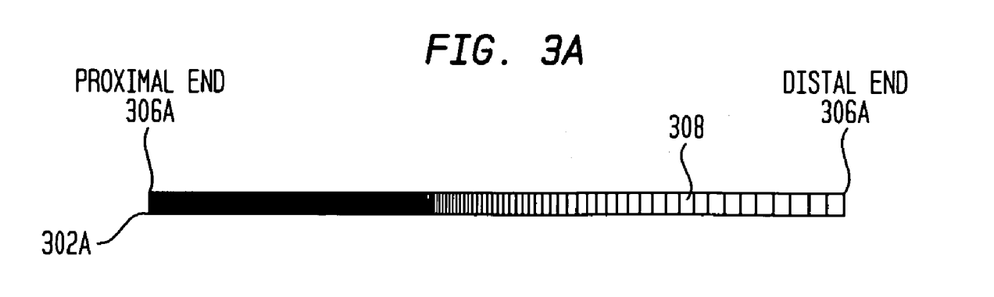
FIG. 3A is a side view of one embodiment of a stiffening element of the present invention suitable for implementation in the carrier member illustrated in FIGS. 2A-2E.
Figure 3B:
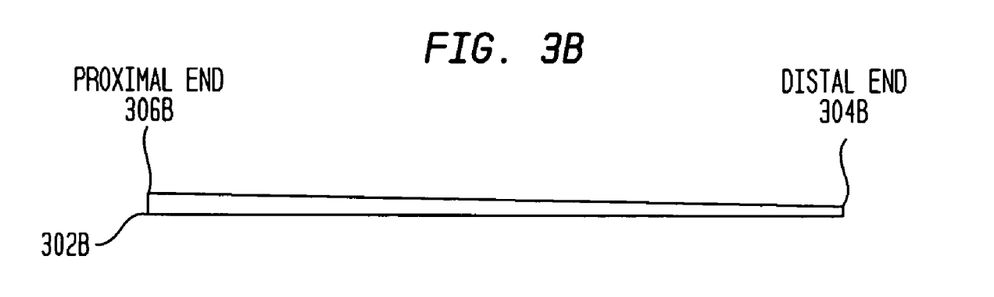
FIG. 3B is a side view of another embodiment of a stiffening element of the present invention suitable for implementation in the carrier member illustrated in FIGS. 2A-2E.
Figure 3C:
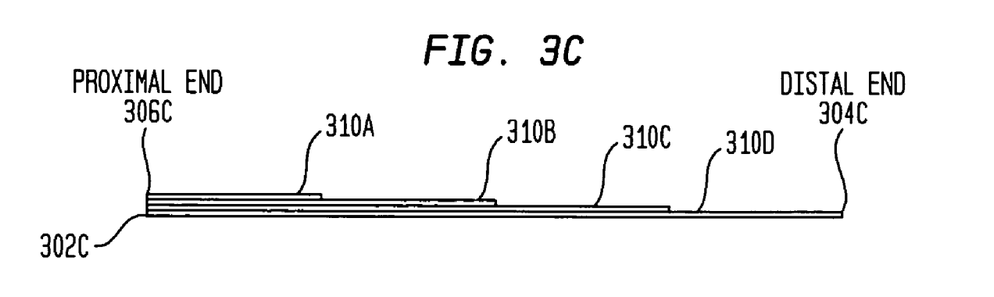
FIG. 3C is a side view of a further embodiment of a stiffening element of the present invention suitable for implementation in the carrier member illustrated in FIGS. 2A-2E.

FIGS. 3A through 3C are side views of different embodiments of stiffening element 208, referred to herein as stiffening element 302A, 302B, and 302C, respectively (generally and collectively referred to as stiffening elements 302). Stiffening elements 302 are configured to be embedded in embodiments of electrode assembly 200, as noted above. In these embodiments, the stiffness or malleability of stiffening member 208 is longitudinally varied so that, for example, that portion of carrier member 202 toward distal end 210 is more flexible than that portion of carrier member 202 toward proximal end 228. Such variability may be attained, for example, by annealing (FIG. 3A), tapering (FIG. 3B) or stepped reduction (FIG. 3C). In these and other embodiments, there preferably is a gradual transition between adjacent segments of stiffening member 208. It should be appreciated that the implemented stiffness is a function of the particular application of cochlear implants and may be different in other applications.

Referring to FIG. 3A, stiffening element 302A is formed of, for example, glass or metal, which is annealed, i.e., subject to a process of heating and slow cooling to toughen and reduce brittleness. In the embodiment shown in FIG. 3A, longitudinally adjacent regions 308 (only one is identified for simplicity) of stiffening member 302A are subject to different annealing process, resulting in regions 308 having a different hardness. In particular, longitudinally successive regions 308 have incrementally greater or less flexibility, depicted in FIG. 3A by successively increasing and decreasing widths of regions 308.

Referring to FIG. 3B, stiffening element 302B is, in this illustrative embodiment, a unitary member that is tapered from its proximal end 306B toward its distal end 304B. The reduced volume of material along successive regions of stiffening element 302B results in a successively decreasing stiffness. It should be appreciated that the rate of taper will dictate the rate of change in flexibility of carrier member 202.

Referring to FIG. 3C, stiffening element 302C is an integrated element comprised of a plurality of elongate strips 310A-310D of differing lengths. Strips 310 may be formed of the same or different material, and may be manufactured to have the same or different stiffness. Strips 310 may be secured to each other or any manner now or later developed. As shown in FIG. 3C, stiffening member 302C has a stepped configuration, due to the different lengths of strips 310. As such, the stiffness provided by stiffening member 302C varies due to the cumulative contribution of each strip 310, which varies along its length. As one of ordinary skill in the art would appreciate, strips 310 need not be arranged to form a continuous series of steps. For example, in embodiments in which the desired flexibility of carrier member 202 does not vary continuously, strips 310 may be configured such that, for example, strip 310B is longer than strip 310C.

Advantageously, stiffening member 208 provides electrode carrier member 202 with sufficient stiffness to allow it to be effectively inserted into cochlea 115, particularly once carrier member 202 encounters some resistance beyond the first turn of the cochlea. A further advantage of the variation in stiffness is to ensure that electrode assembly 200 is suitable for all cochlea sizes. Cochlea sizes, and therefore the basal length, from the round window to the lateral wall of cochlea 115, vary slightly between recipients. The basal length is generally a straight path and is usually in the order of approximately 4 mm to 7 mm. The more flexible distal end of stiffening member 208 ensures that the distal tip of the stiffening member does not impact with the fragile structures of the cochlea. Rather, the distal end deforms allowing carrier member 202 to curve whilst still ensuring the proximal region of the electrode array 200 does not buckle or deform. Preferably, the variable stiffness also ensures that carrier member 202 forms a gradual curve rather than a sharp bend that could result by having a sudden change in mechanical stiffness.

In addition to the embodiments illustrated in FIGS. 3A-3C, the variable stiffness can be achieved by utilizing any number of the following alone or in combination with each other or the embodiments described above: varying the pitch of electrodes 212 as discussed herein; a plurality of stiffening members spaced at various pitches to provide a variable stiffness; use of different materials at various intervals along the length of stiffening member 208; varying dimensions of stiffening element 208 or its component elements, etc. It should also be appreciated that stiffening member 208 may be of any manufacturable cross-section, including round, square, rectangular, oval etc., and use any manufacturable method to provide variable stiffness along its length.

In alternative embodiments, stiffening element 208 extends further into carrier member 202, providing regions of enhanced stiffness where desired. It should be appreciated that the regions of stiffness in the embodiments illustrated in FIGS. 3A-3C, or otherwise, need not vary regularly or consistently. Other embodiments of stiffening member 208 are described in International Application. No. PCT/US06/34010; filed Aug. 31, 2006, which is hereby incorporated by reference herein.

Collar member 204 may serve as a region for grasping electrode assembly 200. Preferably, collar member 204 is constructed and arranged to prevent insertion of carrier member 202 beyond a predetermined maximum depth. This reduces the risk of the surgeon over-inserting electrode assembly 200, which could cause trauma to the delicate structures of cochlea 115. In one preferred embodiment, the predetermined maximum insertion depth 230B of carrier member 202 is approximately 16 mm+/−2 mm.

In the embodiment shown in FIGS. 2A-2E, collar member 204 has a diameter greater than that of carrier member 202. As one of ordinary skill in the art should appreciate, the configuration, orientation and dimensions of collar member 204 can vary depending on the intended implant location and, more generally, on the application of electrode assembly 200. In one embodiment, collar member 204 extends substantially at right angles to longitudinal axis 224 of carrier member 202. In one embodiment, collar member 204 has a length of between about 1.5 mm and about 2.0 mm. In another embodiment, collar member 204 has a length of between about 1.5 mm and about 2.5 mm. Alternatively, collar member 204 may be constructed and arranged generally as described in U.S. patent application Ser. Nos. 10/518,811 and 11/125,171, which are hereby incorporated by reference herein. In certain embodiments, carrier member 202 also includes stiffening member 208, as described above.

In the embodiments illustrated herein, a band 206 is located adjacent collar member 204, circumferentially surrounding carrier member 202 at the junction of carrier member 202 and collar member 204. Band 206 is formed of a material designed to produce a tissue reaction that facilitates tissue attachment to the band, promoting sealing of cochlea 115. In one embodiment, this material primarily contains platinum. This is especially important in preserving residual hearing as prompt sealing of cochlea 115 may greatly reduce the chances of infection of inner ear 103 due to implantation of electrode assembly 200.

In one embodiment, electrodes 212 are half-band electrodes disposed on medial surface 216 of carrier member 202, as shown in FIGS. 2D and 2E. It should be appreciated, however, that any electrode now or later developed suitable for a particular application may be used in alternative embodiments of the invention. For example, in one alternative embodiment, electrodes 212 are banded electrodes extending substantially around carrier member 202. In another alternative embodiment, electrodes 212 do not laterally extend to or around the edges of carrier member 202. Typically, each electrode 212 is arranged orthogonal to longitudinal axis 250 of carrier member 202. It should be appreciated, however, that other relative positioning and orientation may be implemented in alternative embodiments. It should further be appreciated that the quantity of electrodes 212 may vary from as few as one or two to as many as twenty-four or more.

In certain embodiments, at least one electrode 212 has a surface that is at least adjacent medial surface 216 of carrier member 202. Preferably, one or more electrodes 212 has a surface that is collocated with medial surface 216 of carrier member 202, as shown in FIGS. 2D and 2E. In another embodiment, the surfaces of electrodes 212 are raised above or recessed into medial surface 216 of carrier member 202.

Electrodes 212 may be manufactured from a biocompatible conductive material such as platinum, although other materials or combinations of materials may be used. Alternatively, electrodes 212 may be coated with a biocompatible covering that does not interfere with transfer of stimulation signals to cochlea 115.

Figure 2F:
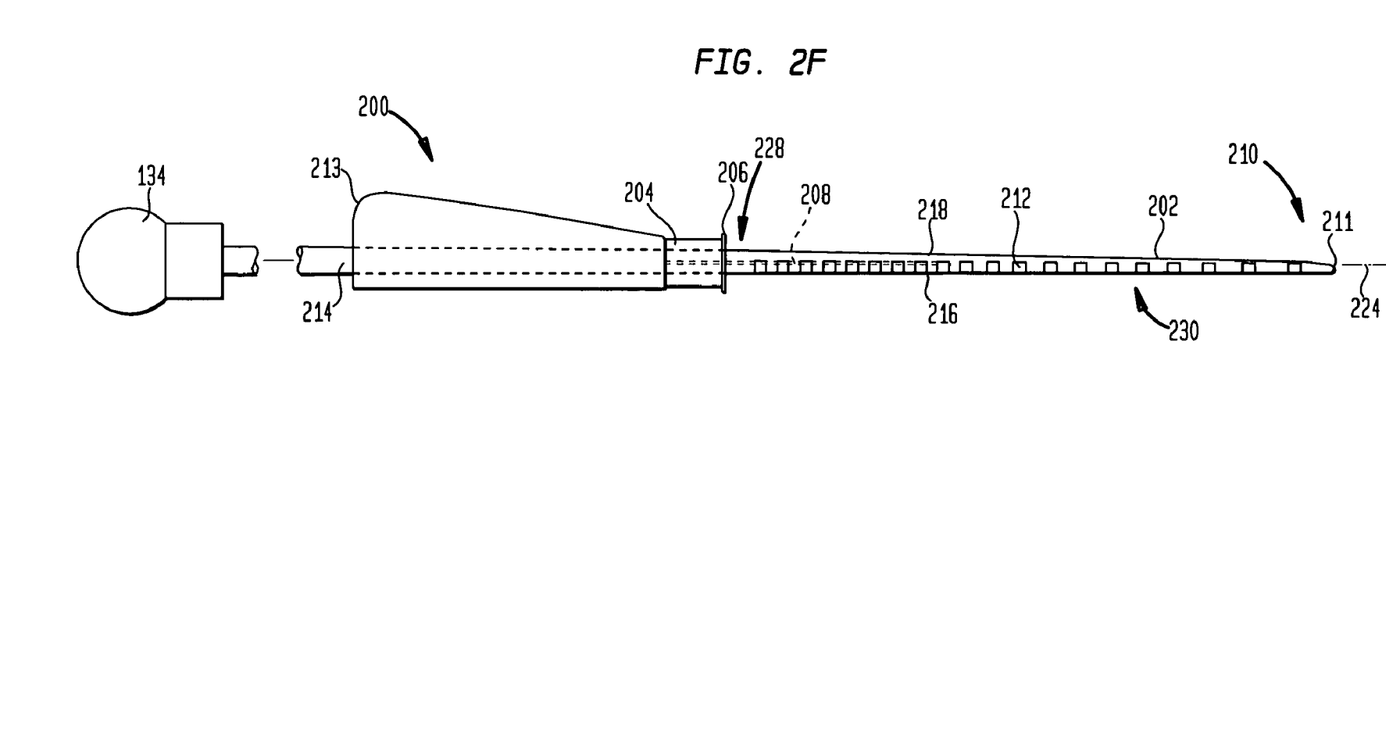
FIG. 2F a side view of an embodiment of an electrode assembly of the invention.

In the embodiments depicted in FIGS. 2A, 2B and 2F, the electrodes are variably spaced to improve flexibility of carrier member 202. In FIGS. 2A and 2B, the electrodes 212 in the basal region are pitched more densely, and the pitch increases toward the center of carrier member 202 and then decreases toward distal end 210 of carrier member 202. The rate of change in electrode pitch between proximal end 228 and the approximate center of carrier member 202 is greater than the more gradual decrease in pitch from the approximate center of carrier member 202 to distal end 210 of carrier member 202.

This provides a distal region 210 that is more flexible that proximal region 228 of carrier member 202, reducing insertion forces to achieve the optimal insertion depth. Furthermore, this also insures that the basal region or high frequency region, which is the area benefited by electrical stimulation in EAS patients, has a higher number, or denser array of stimulating surfaces, providing more specificity of stimulation, and also greater pitch matching of electrodes 212.

Figure 4A:
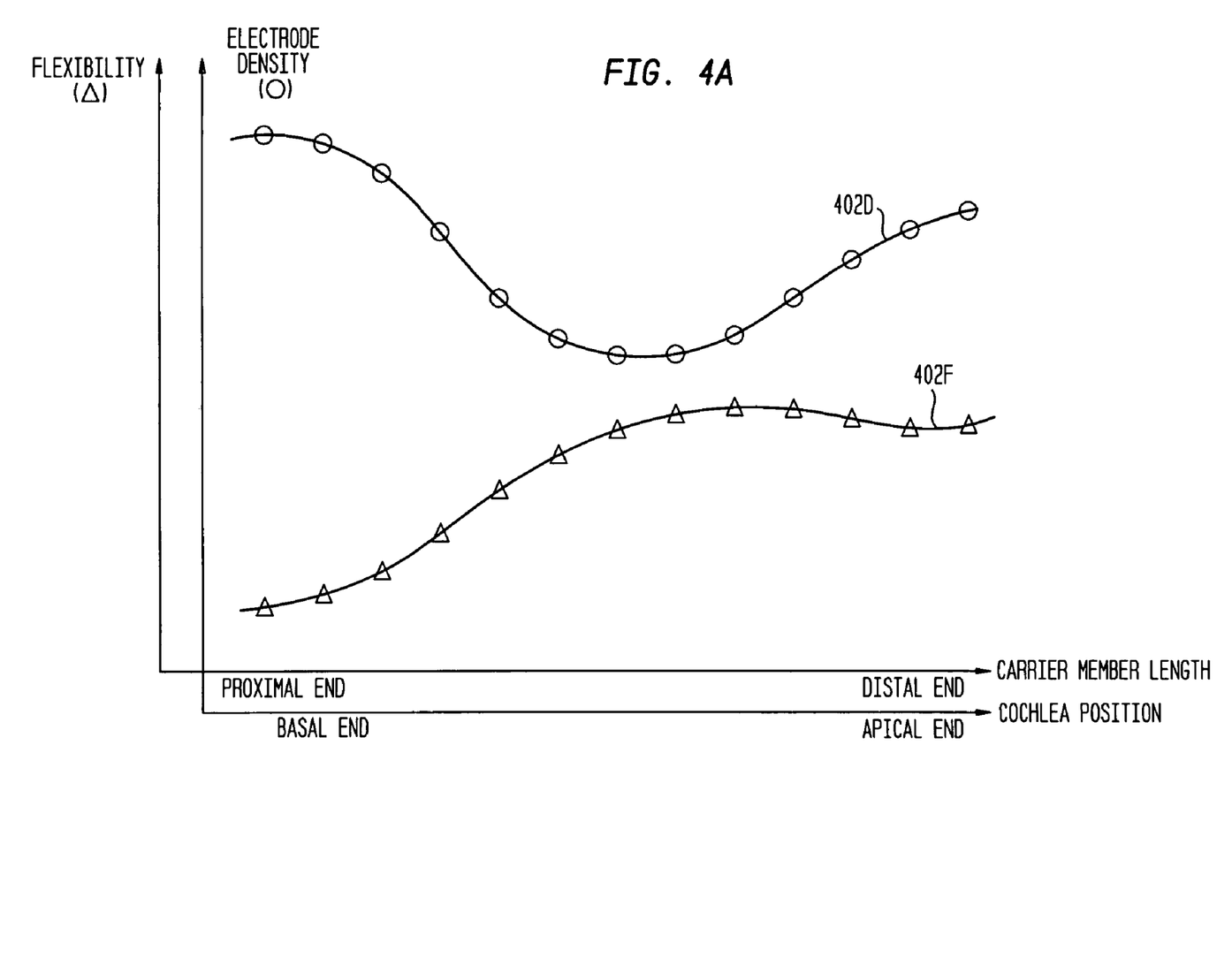
FIG. 4A is a graph illustrating the relationship between the variable electrode density and flexibility for the embodiment of the present invention illustrated in FIGS. 2A and 2B.

FIG. 4A is a graph illustrating the relationship between the variable electrode density and flexibility for the embodiment of the present invention illustrated in FIGS. 2A and 2B. In FIG. 4A, the horizontal axis represents carrier member length 230B (FIG. 2B) and the position along cochlea 115 (FIG. 1). When implanted, proximal end 228 of carrier member 202 resides in the vicinity of basal end of cochlea 115, while distal end 210 of carrier member 202 resides in the vicinity of apical end of cochlea 115. The vertical axis represents the density of electrodes 212 and corresponding flexibility of carrier member 202.

As noted, in FIGS. 2A and 2B, the pitch or spacing of electrodes 212 in the basal region is small; that is, the density of the electrodes is greater. The pitch increases toward the center of carrier member 202 and then decreases toward distal end 210 of carrier member 202. Thus, the density decreases toward the center of carrier member 202 and increases toward the distal end, as shown by graph line 402D. As shown in FIG. 4A, the rate of change in electrode pitch between proximal end 228 and the approximate center of carrier member 202 is greater than the more gradual decrease in pitch from the approximate center of carrier member 202 to distal end 210 of carrier member 202.

Figure 4B:
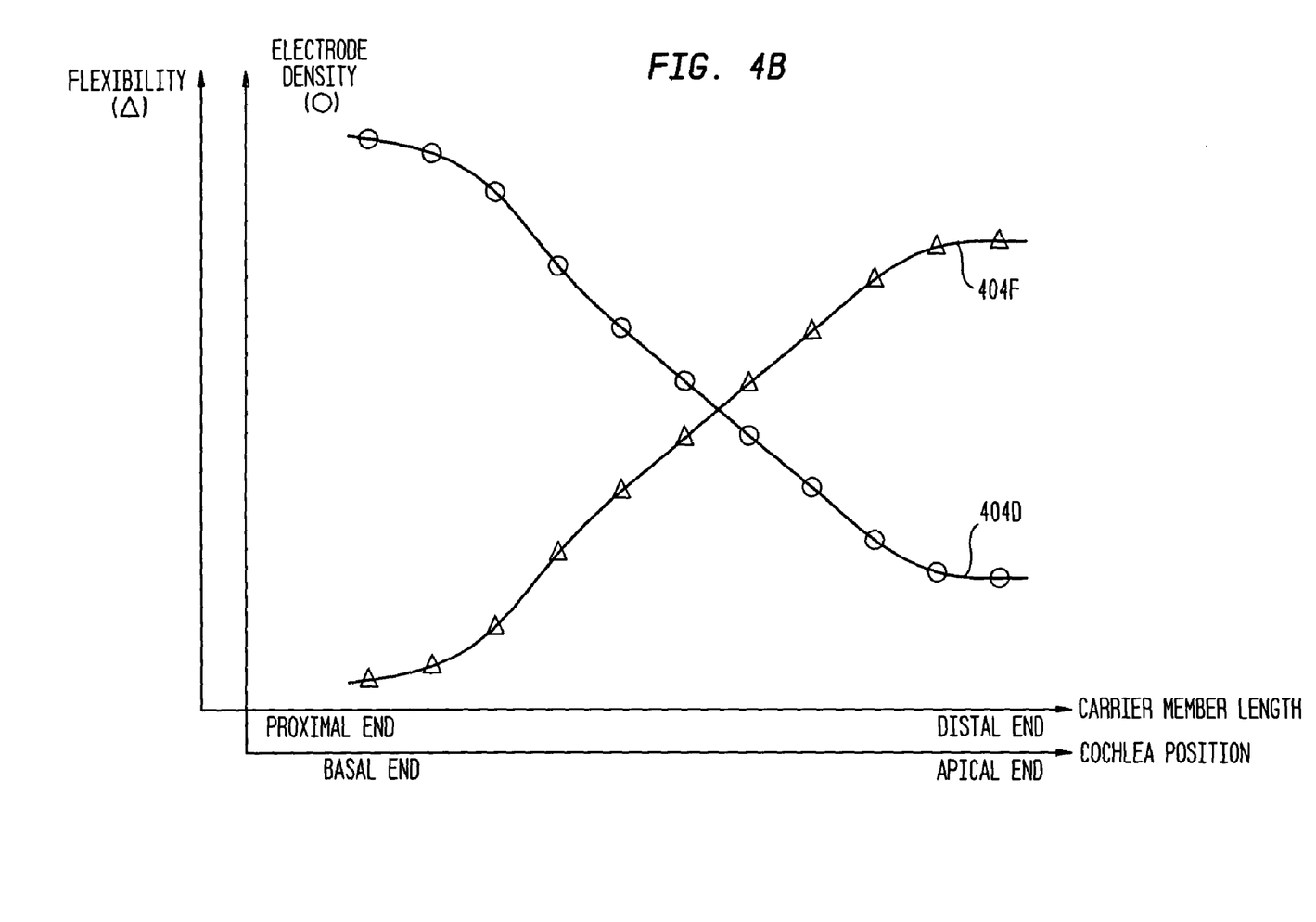
FIG. 4B is a graph illustrating the relationship between the variable electrode density and flexibility for the embodiment of the present invention illustrated in FIG. 2F.

Returning to FIG. 2F is a side view of another embodiment of an electrode assembly of the present invention. In this embodiment, the electrode pitch continues to increase from proximal region 228 to distal region 210. As shown in corresponding FIG. 4B, this provides a range of flexibility 404F that increases steadily along the length of carrier member 202, with proximal region 228 having increased density 404D and decreased flexibility 404F and distal region 210 having decreased density 404D and increased flexibility 404F.

The greater flexibility in distal region 210 As compared with proximal region 228 reduces the insertion forces required to achieve the optimal insertion depth. This also insures that the basal (high frequency) region of cochlea 115, which is the area benefited by electrical stimulation in EAS patients, has a greater density of electrodes, providing more specificity of stimulation, and also greater pitch matching of electrodes 212.

As one of ordinary skill in the art would appreciate, the type, dimensions and other characteristics of electrodes 212 and other elements of the electrode carrier member may be altered in concert with the electrode spacing or pitch to achieve a desired level of flexibility along the length of electrode carrier 202.

The increased density of electrodes 212 in proximal region 228 of electrode carrier member 202 provides additional stiffness sufficient to assist in the prevention of buckling of carrier member 202 during insertion into cochlea 115. This allows carrier member 202 and electrodes 212 to be introduced into cochlea 115 without deformation, thereby enabling full insertion without application of unnecessary force which may damage the delicate structures of the cochlear.

Additionally, the density of electrodes 212 in proximal region 228 of carrier member 202 causes the basal electrode contacts 212 to be positioned closer to the inner wall of cochlea 115, as generally a straight electrode will take a more lateral position in the basal region. As a result, the distance from the stimulating surface of carrier member 202 to the cochlear nerve is shorter. It is anticipated that this will provide similar benefits in the basal region as a perimodiolar electrode, such as the perimodiolar electrode described in U.S. Pat. No. 6,421,569.

As noted, in certain embodiments, carrier member 202 also includes a stiffening member 208 as described above. In certain embodiments, stiffening member 208 may be longitudinally varied in concert with the variable pitch of electrodes 212 to achieve a desired flexibility along the length of carrier member 202.

An advantage of the variation in stiffness is to ensure that electrode assembly 200 is suitable for all sizes of cochleas. Cochlea sizes, and therefore the basal length, from the round window to the lateral wall of cochlea 115, vary slightly between patients. The basal length is generally a straight path and is usually in the order of 4 mm to 7 mm. The more flexible distal end 210 of carrier member 202 ensures that the distal tip of the stiffening member does not impact with the fragile structures of the cochlear. Rather, the distal end deforms allowing the carrier member 202 to curve whilst still ensuring the proximal region of the electrode array 200 does not buckle or deform. Preferably, the variable stiffness also ensures that carrier member 202 forms a gradual curve rather than a sharp bend that could result by having a sudden change in mechanical stiffness.

Returning to FIG. 2A, collar member 212 serves as both a region for grasping electrode assembly 200 and also acts to prevent insertion of carrier member 202 beyond a predetermined maximum depth to reduce the risk of the surgeon over-inserting electrode assembly 200, which could otherwise cause trauma to the delicate structures of cochlea 115. In one embodiment described in the noted concurrently-filed US Provisional Patent Applications, incorporated by reference elsewhere herein, the predetermined maximum depth is approximately 16 mm+/−2 mm.

In the embodiment shown in FIG. 2A, collar member 212 has a diameter slightly greater than that of carrier member 202. As one of ordinary skill in the art should appreciate, the configuration, orientation and dimensions of collar member 212 can vary depending on the intended application of electrode assembly 200. In one embodiment, collar member 212 extends substantially at right angles to longitudinal axis 224 of carrier member 202. In another embodiment of the present invention, collar member 212 has a length of between about 1.5 and about 2.0 mm. Alternatively, collar member 204 may be constructed and arranged generally as described in U.S. patent application Ser. Nos. 10/518,811 and 11/125,171, which are hereby incorporated by reference herein in their entireties.

Referring to FIGS. 2A, 2B, 2D and 2E, in certain embodiments, electrode carrier member 202 is longitudinally-tapered. As such, the dimensions of carrier member 202 at section line 2D-2D are greater that the dimensions of carrier member 202 at section line 2E-2E, as shown in FIGS. 2D and 2E. This tapered configuration may, in certain embodiments, result in a continuous gradual taper to tip region 210. Tip region 210 facilitates the insertion of carrier member 202 into a recipient's cochlea 115. In one embodiment, tip member region 210 comprises a taper which slopes from a lateral surface 218 rearward and inward toward the medial surface 216. Such a tapered tip region 210 aids the coiling of carrier member 200 and further helps prevent damage to the delicate structures of the cochlea. FIG. 2C, which is a cross-sectional view of collar member 212, shows a marker 304 to facilitate orientation and a lumen through which wires 252 and stiffening element 208 extend.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

All documents, patents, journal articles and other materials cited in the present application are hereby incorporated by reference.

What is claimed is:

1. An electrode assembly for use in a prosthetic hearing implant, comprising:
   an elongate carrier member for implantation into the cochlea, the carrier member having a proximal end adapted to be positioned in a basal region of the cochlea, and a distal end adapted to be positioned in an apical region of the cochlea; and
   a plurality of electrodes disposed along a longitudinal surface of said carrier member, wherein longitudinally adjacent of electrodes have a predetermined longitudinal spacing to attain a desired flexibility along said length of said carrier member, a first set of adjacent electrodes that are more closely spaced than a second set of adjacent electrodes, said first set of adjacent electrodes being located near said proximal end of said carrier member, and said second set of adjacent electrodes being located near said distal end of said carrier member.

2. The electrode assembly of claim 1, further comprising:
   a stiffening member embedded in at least a proximal region of carrier member, wherein said stiffening member has a malleability that varies longitudinally along a length of said stiffening member.

3. The electrode assembly of claim 2, wherein said spacing of said plurality of electrodes and said variable malleability are selected to achieve the desired flexibility along the length of said carrier member.

4. The electrode assembly of claim 1, further comprising:
   a laterally-extending collar member connected to said proximal end of said carrier member and configured to abut the cochlea when said carrier member is implanted at a maximum insertion depth, and to prevent further insertion of said carrier member into the cochlea.

5. The electrode assembly of claim 1, wherein said carrier member is longitudinally-tapered, wherein said proximal end of said carrier member has greater dimensions than said distal end of said carrier member.

6. The electrode assembly of claim 4, further comprising:
   a band circumferentially surrounding said proximal end of said carrier member, said band formed of a material that produces a tissue reaction that facilitates tissue attachment to the band.

7. The electrode assembly of claim 1, wherein said electrode assembly further comprises:
   a tapered tip region disposed at said distal end of said carrier member.

8. The electrode assembly of claim 4, further comprising:
   a holding member having a distal end connected to said proximal end of said collar member, wherein said holding member is configured to provide a surface for manual control of said electrode assembly.

9. The electrode assembly of claim 4, further comprising:
   an elongate lead connected to said proximal end of said collar member, said lead physically and electrically connecting said electrode assembly an implanted stimulator unit.

10. The electrode assembly of claim 9, wherein said lead is continuous with no intermediate electrical connectors between said electrode assembly and the stimulator unit.

11. The electrode assembly of claim 1, wherein said plurality of electrodes are positioned along said carrier member so as to align with predetermined regions of a tonotopically mapped cochlea.

12. The electrode assembly of claim 1, wherein said carrier member has opposing medial and lateral longitudinal surfaces, wherein when implanted, said medial surface faces toward the center of the cochlea and said lateral surface faces toward the exterior of the cochlea, wherein at least one of said plurality of electrodes has a surface that is collocated with said medial surface of said carrier member.

13. The electrode assembly of claim 1, wherein each of said plurality of electrodes is electrically connected to at least one multi- or single-filament wire embedded within said carrier member.

14. The electrode assembly of claim 13, wherein said wires are embedded in a volumetric core of said carrier member.

15. The electrode assembly of claim 13, wherein said wires are located at or near surfaces of said carrier member.

16. The electrode assembly of claim 15, wherein said wires are located in different regions of said carrier member to facilitate curvature or to maintain orientation of said carrier member once said carrier member is implanted.

* * * * *